(12) United States Patent
Kandori et al.

(10) Patent No.: US 7,798,981 B2
(45) Date of Patent: Sep. 21, 2010

(54) LIVING BODY INSPECTION APPARATUS

(75) Inventors: Akihiko Kandori, Kokubunji (JP); Tsuyoshi Miyashita, Fuchu (JP); Keiji Tsukada, Okayama (JP); Kenko Uchida, Tokyo (JP); Hideo Kawaguchi, Hatoyama (JP); Minoru Sakairi, Tokorozawa (JP)

(73) Assignee: Hitachi, Ltd., Tokyo (JP)

( * ) Notice: Subject to any disclaimer, the term of this patent is extended or adjusted under 35 U.S.C. 154(b) by 130 days.

(21) Appl. No.: 12/267,056

(22) Filed: Nov. 7, 2008

(65) Prior Publication Data
US 2009/0069663 A1    Mar. 12, 2009

Related U.S. Application Data

(63) Continuation of application No. 10/788,377, filed on Mar. 1, 2004, now Pat. No. 7,455,648.

(30) Foreign Application Priority Data

Sep. 22, 2003   (JP)   ............................... 2003-329299

(51) Int. Cl.
*A61B 5/103* (2006.01)
*A61B 5/05* (2006.01)
(52) U.S. Cl. .................. 600/595; 600/407; 600/587
(58) Field of Classification Search ............ 600/407, 600/587, 595; 324/207.17, 225–226; 128/782
See application file for complete search history.

(56) References Cited

U.S. PATENT DOCUMENTS

| | | |
|---|---|---|
| 5,744,953 A | 4/1998 | Hansen |
| 6,172,499 B1 | 1/2001 | Ashe |
| 6,416,485 B1 | 7/2002 | Rovetta et al. |
| 2004/0210166 A1* | 10/2004 | Soh et al. ............... 600/595 |

FOREIGN PATENT DOCUMENTS

| | | |
|---|---|---|
| JP | 5-5784 | 1/1993 |
| JP | 2003-15810 | 7/2003 |

OTHER PUBLICATIONS

Movement Disorder, vol. 15, No. 1, 2000, pp. 36-47.
Movement Disorder, vol. 12, No. 5, 1997, pp. 665-676.

(Continued)

*Primary Examiner*—Eric F Winakur
*Assistant Examiner*—Michael T Rozanski
(74) *Attorney, Agent, or Firm*—Mattingly & Malur, P.C.

(57) ABSTRACT

A living body inspection apparatus including an oscillation coil which passes an AC current, a detection coil which detects an AC magnetic field generated from the detection coil, an amplification circuit which amplifies a voltage generated by the magnetic field induced by the detection coil, a detecting unit for detecting the output signal of the amplification circuit, a low pass filter to which the output signal of the detecting unit is input, a unit for setting the oscillation coil and detection coil in first and second regions of the living body, a recording unit for recording the output of the low pass filter while the first region and the second region of the living body are moving and a displaying unit for displaying the data recorded in the recording unit or results of analysis of the recorded data.

7 Claims, 15 Drawing Sheets

OTHER PUBLICATIONS

A. Jobbagy et al, "Movement Analysis of Parkinsonians," Proceedings of the 22nd Annual EMBS International Conference, Jul. 23-28, IEEE, 2000, pp. 821-824.

V. Rajaraman et al, "A Novel Quantitive Method for 3D Measurement of Parkinsonian Tremor," Feb. 2000, vol. III, No. 2, pp. 338-343.

K. Norman et al, "The Measurement of Tremor Using a Velocity Transducer: Comparison to Simultaneous Recordings Using Transducers of Displacement, Acceleration and Muscle Activity," Oct. 15, 1999, vol. 92, No. 1-2, pp. 41-54.

* cited by examiner

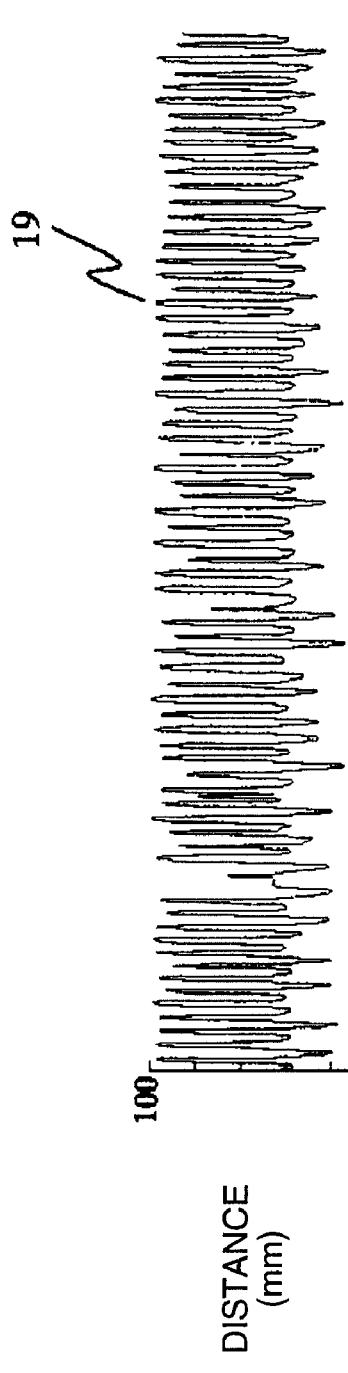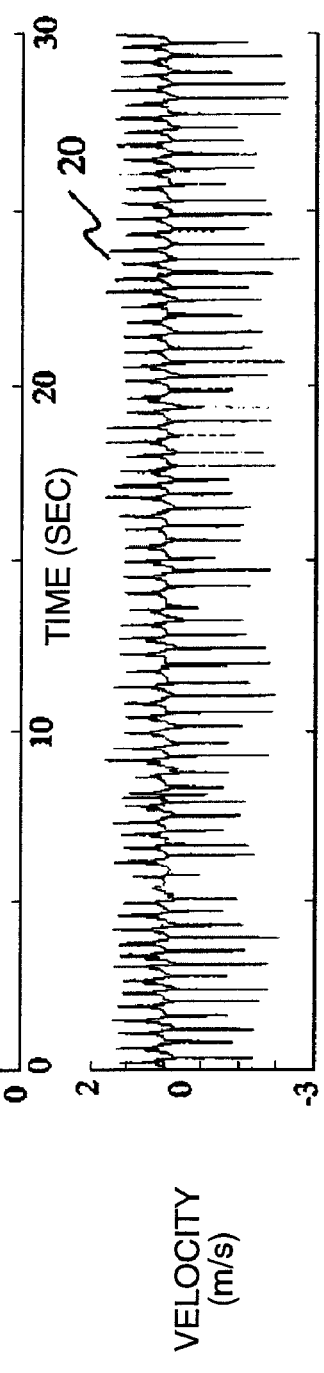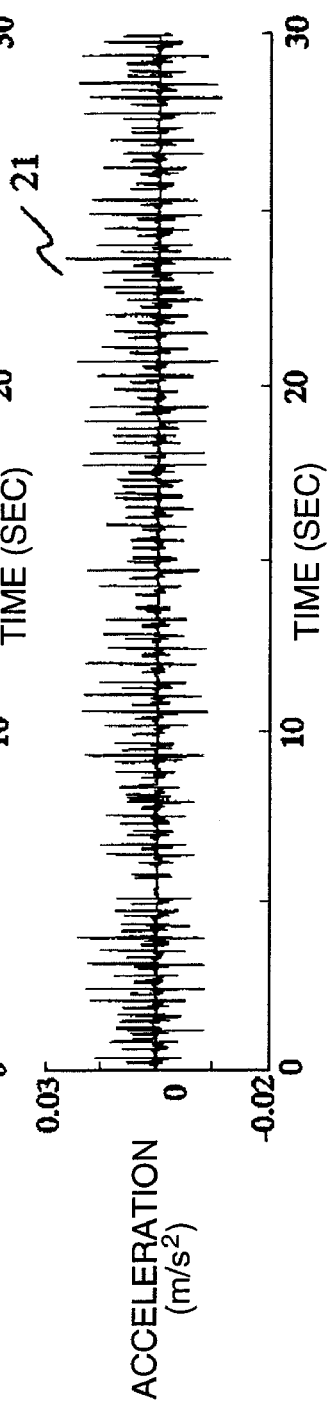
FIG. 6A
FIG. 6B
FIG. 6C

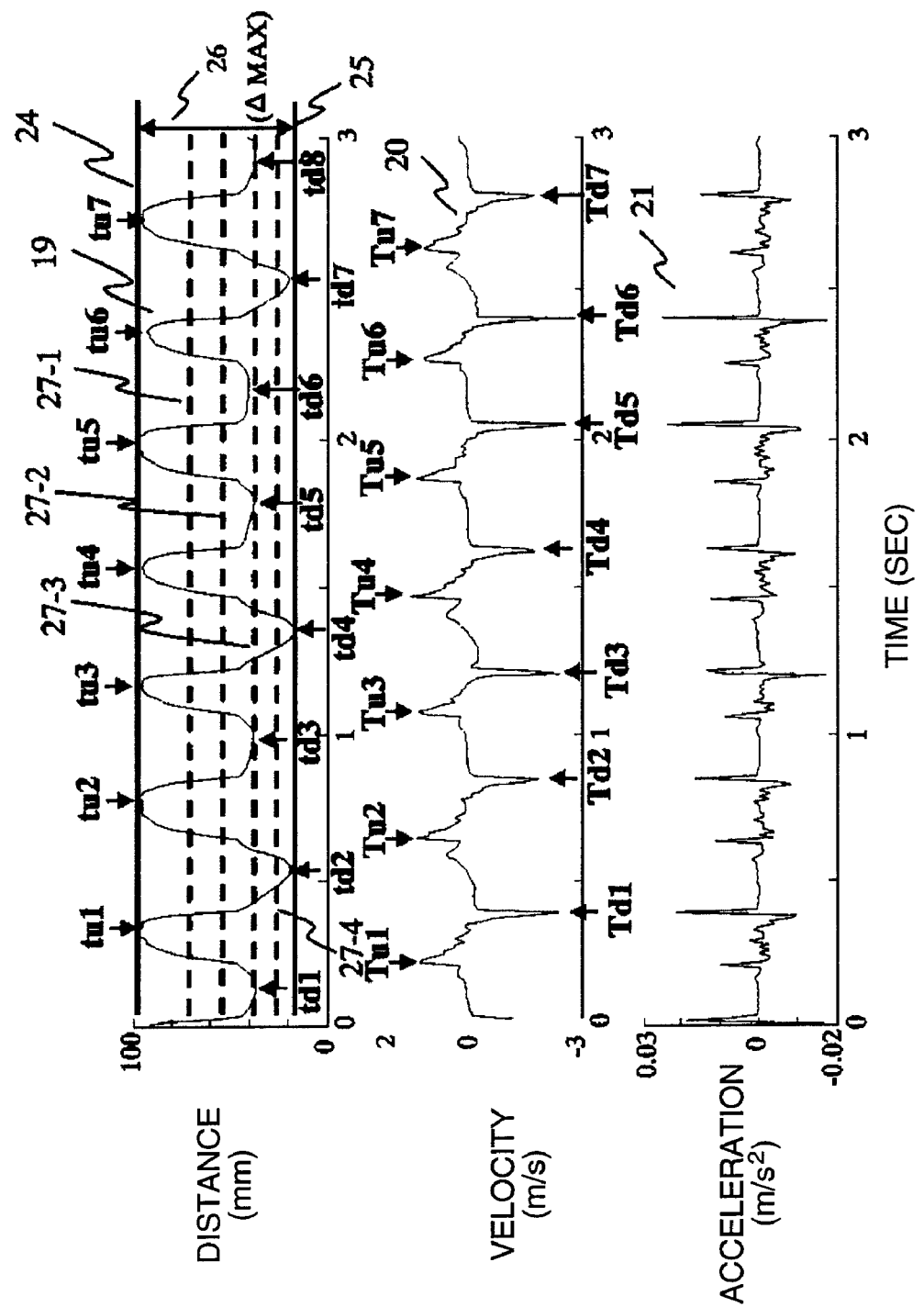

FIG. 10

AMPLITUDE IRREGULARITY

| AMPLITUDE THRESHOLD | TAPPING PROBABILITY |
|---|---|
| 90% | 15/30 (50%) |
| 70% | 18/30 (60%) |
| 50% | 25/30 (83%) |
| 30% | 27/30 (90%) |

$$\text{AVERAGE TAPPING INTENSITY} = \frac{\text{TOTAL AREA OF ACCELERATION}}{\text{TAPPING COUNT}}$$

30

HESITATION RATE

| PARAMETER | HESITATION RATE |
|---|---|
| $\Delta D2 / \Delta D1$ | 75% |
| $\Delta V2 / \Delta V1$ | 84% |
| $\Delta A2 / \Delta A1$ | 83% |

LIVING BODY INSPECTION APPARATUS

This is a continuation application of U.S. Ser. No. 10/788,377, filed Mar. 1, 2004 now U.S. Pat. No. 7,455,648, which is hereby incorporated by reference into this application.

BACKGROUND OF THE INVENTION

The present invention relates to a living body inspection apparatus for detecting movement of regions of a living body using a coil which generates magnetism.

A Parkinson's disease is a cerebropathy having a new structure caused by chronic degeneration of cranial nerve. Though it is a cerebropathy, no characteristic symptoms are found in a blood test or observation with diagnostic imaging. It is therefore an actual situation that the severity of Parkinson's disease is decided and a dosage is adjusted according to clinical symptoms (trembling, tension of muscles, abnormality of posture, etc.) and complaint of the patient.

To quantitatively decide the severity of Parkinson's disease, a method of tapping the keyboard of a computer has been studied so far and this method allows ON/OFF movement of fingers to be evaluated simply (e.g., see Movement Disorder, vol. 15, No. 1, 2000, pp. 36-47).

In addition to the method of keyboard tapping, a technique of measuring timing of pressing buttons is reported and an apparatus for pressing buttons is simple and allows ON/OFF movement of fingers to be evaluated simply as in the case of using a keyboard (e.g., see U.S. Pat. No. 6,416,485).

On the other hand, as a method of evaluating movement of fingers in an analog form, a method using an optoelectronic camera system (system for detecting movement of fingers from a camera image) is reported (e.g., see Movement Disorder, vol. 12, No. 5, 1997, pp. 665-676).

As an input apparatus for a sign language, a method of detecting movement of fingers by exciting a primary winding and detecting movement of the positions of a magnetic response member and a secondary winding is reported (e.g., see JP-A-2003-15810). The technique described in JP-A-2003-15810 allows bending and stretching of fingers to be detected. According to the technique described in JP-A-2003-15810, an oscillation coil is placed at each finger tip, a detection coil is placed on the palm of a hand, AC currents of different frequencies are passed through the respective oscillation coils and a frequency detection circuit detects an induced electromotive force obtained from the detection coil on the palm of the hand to find which finger touches the palm of the hand.

In the field of a metal detection apparatus, a method of detecting a metal object moving between a fixed excitation circuit and a detection coil is reported (e.g., see JP-A-5-5784). According to the method described in JP-A-5-5784, an amount of variation due to an eddy current is detected by a detection circuit and detected through a low pass filter.

To quantitatively decide the severity of Parkinson's disease, it is necessary to observe coordinated movement that two or more regions of a living body (two fingers or two lips, etc.) try to move simultaneously. The keyboard tapping method described in Movement Disorder, vol. 15, No. 1, 2000, pp. 36-47 and the method of pressing buttons described in U.S. Pat. No. 6,416,485 can only obtain digital ON/OFF information and cannot detect the degree of stretching of fingers. The methods described in Movement Disorder, vol. 15, No. 1, 2000, pp. 36-47 and U.S. Pat. No. 6,416,485 cannot sufficiently decide the stiffness of movement of fingers which is characteristic of Parkinson's disease.

The method described in Movement Disorder, vol. 12, No. 5, 1997, pp. 665-676 allows collection of analog data about the degree of stretching of fingers but since it detects movement of fingers from images, data processing is complicated and takes much detection time. On top of this, it also results in a large system which is costly.

According to the technique described in JP-A-2003-15810, the information obtained by the frequency detection circuit is binary information of ON and OFF indicating whether the palm of the hand is touched or not and cannot sufficiently decide stiffness of movement of fingers which is characteristic of Parkinson's disease.

The method described in JP-A-5-5784 is principally intended to detect an amount of change of movement of metal and acquires no information on movement of a living body.

In order to solve the above described problems, it is an object of the present invention to provide a living body inspection apparatus for detecting movement of regions of a living body in a simple structure capable of continuously detecting signals caused by movement of two or more regions of the living body (coordinated movement).

SUMMARY OF THE INVENTION

The living body inspection apparatus of the present invention comprises an AC generation circuit which generates an AC voltage having a predetermined frequency, converting means for converting the AC voltage output from the AC generation circuit to an AC current, an oscillation coil which passes the AC current output from the converting means, a detection coil which detects an AC magnetic field generated from the oscillation coil, an amplification circuit which amplifies a voltage generated by the magnetic field detected by the detection coil, demodulating means for detecting a signal with the same frequency as that of the AC generation circuit or a double harmonic frequency from the output signal of the amplification circuit, a low pass filter to which the demodulated signal of the detecting means is input, means for setting the detection coil in a first region of the living body, means for setting the detection coil in a second region of the living body, recording means for recording the output of the low pass filter while the first region and the second region of the living body are moving and displaying means for displaying the data recorded in the recording means or results of an analysis of the recorded data. The oscillation coil and the detection coil are attached to different fingers.

Furthermore, the living body inspection apparatus of the present invention further comprises calculating means for converting a voltage value of the data recorded in the recording means to a distance corresponding to the distance between the first region and the second region and displays the distance on the displaying means.

Furthermore, the living body inspection apparatus of the present invention further comprises calculating means for converting a voltage value of the data recorded in the recording means to a distance corresponding to the distance between the first region and the second region, primary differentiating means for primary differentiating the waveform of the voltage value of the data recorded in the recording means or the waveform obtained by the calculating means and secondary differentiating means for secondary differentiating the waveform of the voltage value of the data recorded in the recording means or the waveform obtained by the calculating means.

Furthermore, the living body inspection apparatus of the present invention further comprises timing detecting means for detecting tapping timing from the output waveform of the primary differentiating means and displays a waveform of the detected timing.

Furthermore, the living body inspection apparatus of the present invention further comprises transmitting means for transmitting the tapping timing to an examinee.

Furthermore, the living body inspection apparatus of the present invention further comprises diagnostic supporting means for measuring coordinated movement of the living body and detecting abnormalities in the brain.

Furthermore, the living body inspection apparatus of the present invention further comprises means for detecting a signal corresponding to an amount of change in the relative distance between two regions of the living body and means for displaying the detected amount of change as a signal indicating the coordinated movement of the living body, and acquires information on abnormalities of the brain activities.

According to the living body inspection apparatus of the present invention, it is possible to realize quantitative measurement of a physical amount corresponding to a relative distance between two regions of the living body, detect signals generated by movements (coordinated movements) of the two regions of the living body continuously and thereby quantify the coordinated movements. Therefore, it is possible to quantitatively determine the motor function accompanying cerebropathy such as Parkinson's disease.

Other objects, features and advantages of the invention will become apparent from the following description of the embodiments of the invention taken in conjunction with the accompanying drawings.

BRIEF DESCRIPTION OF THE DRAWINGS

FIGS. 6A to 6C illustrate measured data and an example of the result of signal processing according to the embodiment of the present invention;

FIGS. 9A to 9C illustrate a technique of detecting amplitude irregularity in tapping from a distance waveform according to the embodiment of the present invention;

FIG. 10 illustrates a screen example showing amplitude irregularity according to the embodiment of the present invention;

FIG. 11 illustrates an example of the display screen of average tapping intensity according to the embodiment of the present invention;

DESCRIPTION OF THE EMBODIMENTS

With reference now to the attached drawings, embodiments of the present invention will be explained in detail below.

Figure 1:
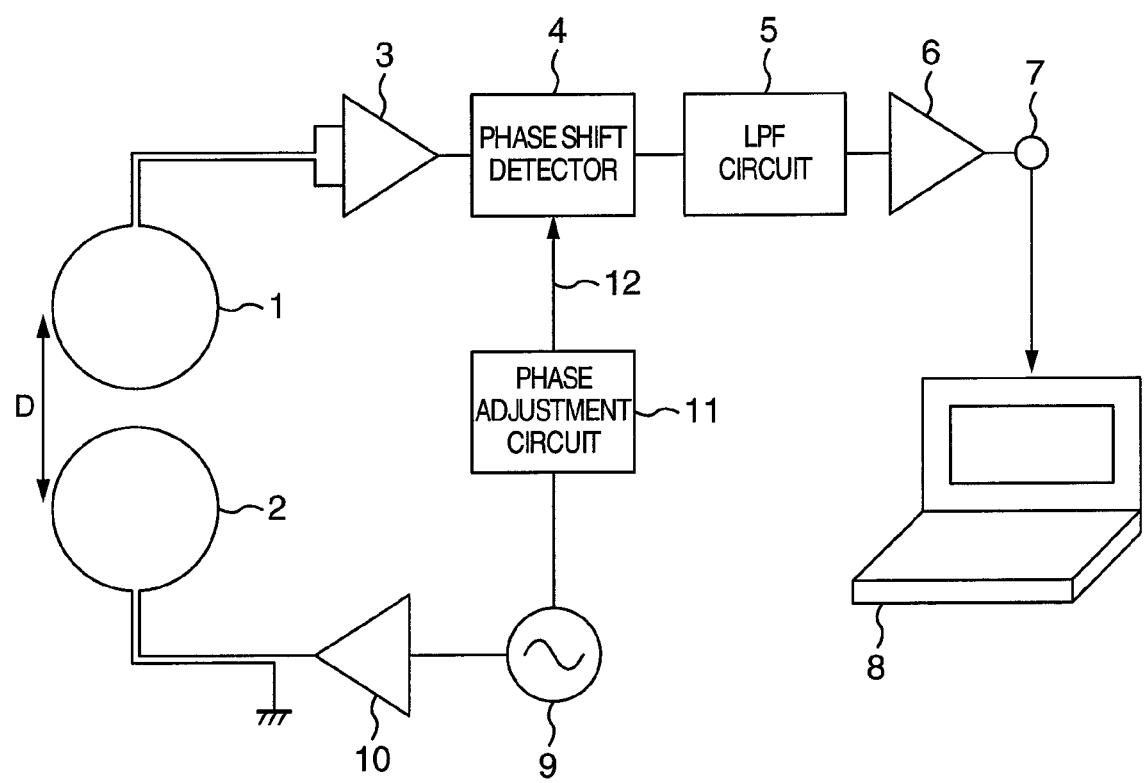
FIG. 1 illustrates a configuration example of a living body inspection apparatus according to an embodiment of the present invention.

FIG. 1 illustrates a configuration example of a living body inspection apparatus according to an embodiment of the present invention.

An AC generation circuit 9 generates an AC voltage having a predetermined frequency (e.g., 20 kHz). The AC voltage having the predetermined frequency generated is converted to an AC current having a predetermined frequency by a current generation amplifier circuit 10. The AC current is input to an oscillation coil 2 attached to a living body.

A magnetic field generated in the oscillation coil 2 induces a voltage in a detection coil 1 attached to the living body. The induced voltage (having the same frequency as the AC voltage having the predetermined frequency generated by the AC generation circuit 9) is amplified by a preamplifier circuit 3. The amplified signal is input to a phase shift detector 4. The phase shift detector 4 carries out detection with a predetermined frequency or double frequency generated by the AC generation circuit 9, and therefore the phase of the output of the AC generation circuit 9 is adjusted by a phase adjustment circuit 11 and then input to a reference signal input terminal of the phase shift detector 4 as a reference signal 12.

When detection is performed with a frequency double the predetermined frequency, the phase adjustment circuit 11 is not always necessary. A simple circuit for detection with the double frequency is constructed by setting the predetermined frequency of the AC generation circuit 9 to a double frequency, converting it to a half frequency by a frequency divider, inputting it to the current generation amplifier circuit 10 and inputting a signal with a frequency double the predetermined frequency of the AC generation circuit 9 to the reference signal input terminal of the phase shift detector 4 as the reference signal 12.

The output of the phase shift detector 4 passes through a low pass filter circuit 5 and is amplified by an amplifier circuit 6 to obtain a desired voltage and an output signal 7 is obtained in this way. The output signal 7 is converted to digital data by an analog/digital conversion board (AD board) built in a computer 8 and input to the computer 8.

In the above described configuration example, a voltage corresponding to a relative distance D between the detection coil 1 and oscillation coil 2 attached to the living body appears at the output signal 7.

Figure 2:
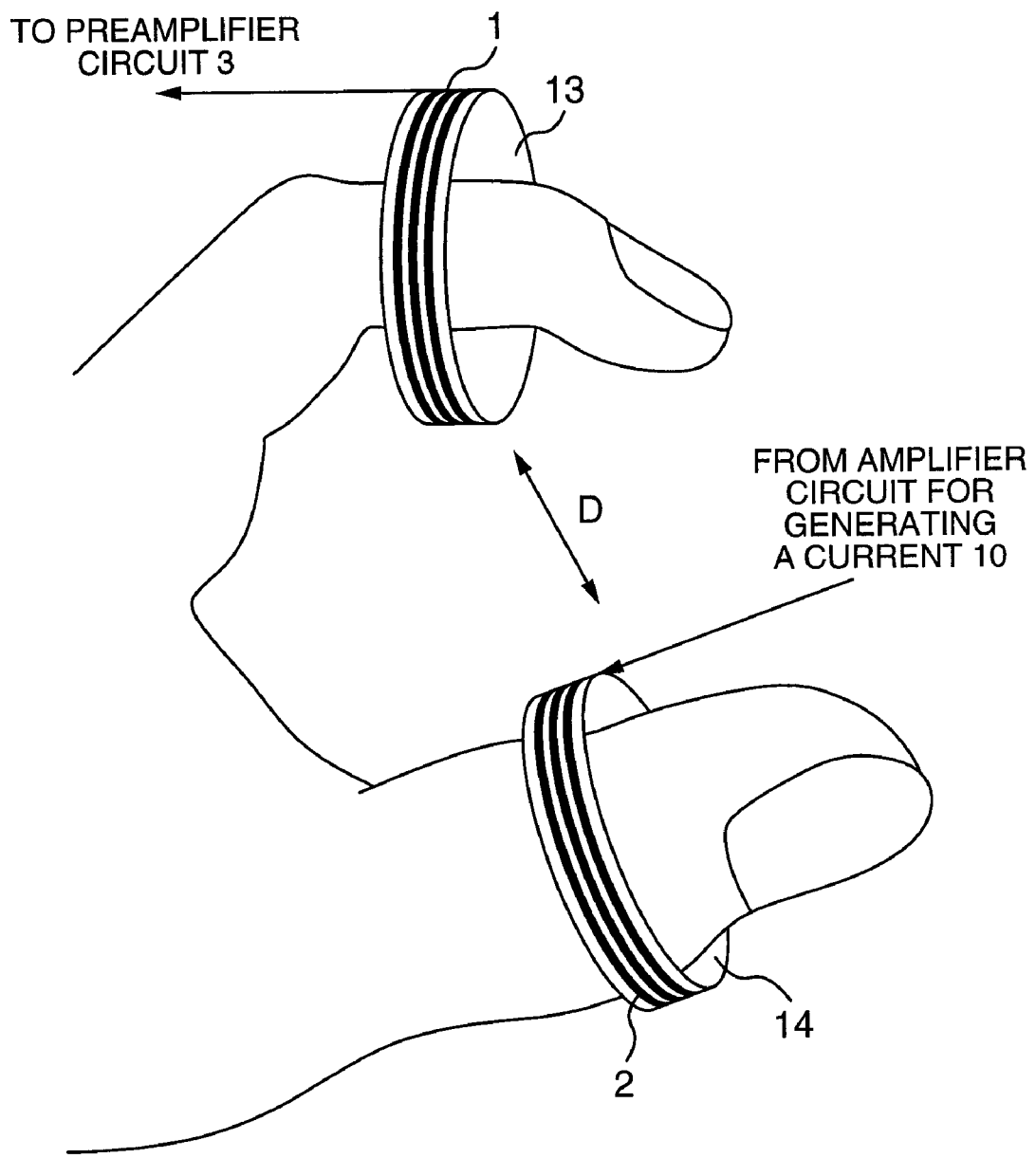
FIG. 2 illustrates a first method of attaching a detection coil and oscillation coil according to the embodiment of the present invention to the living body.

FIG. 2 illustrates a first method of attaching the detection coil and oscillation coil to the living body according to the embodiment of the present invention.

The oscillation coil 2 is put on a thumb and the detection coil 1 is put on a forefinger. The oscillation coil 2 is wound around a coil attaching member 14 and connected to the current generation amplifier 10 shown in FIG. 1. The detection coil 1 is wound around a coil attaching member 13 and connected to the preamplifier circuit 3 shown in FIG. 1. Furthermore, the inner surfaces of the attaching members 13 and 14 are provided with a cushioning material such as rubber and sponge which contacts the finger so as to absorb individual differences in size (thickness) of fingers.

Figure 3:
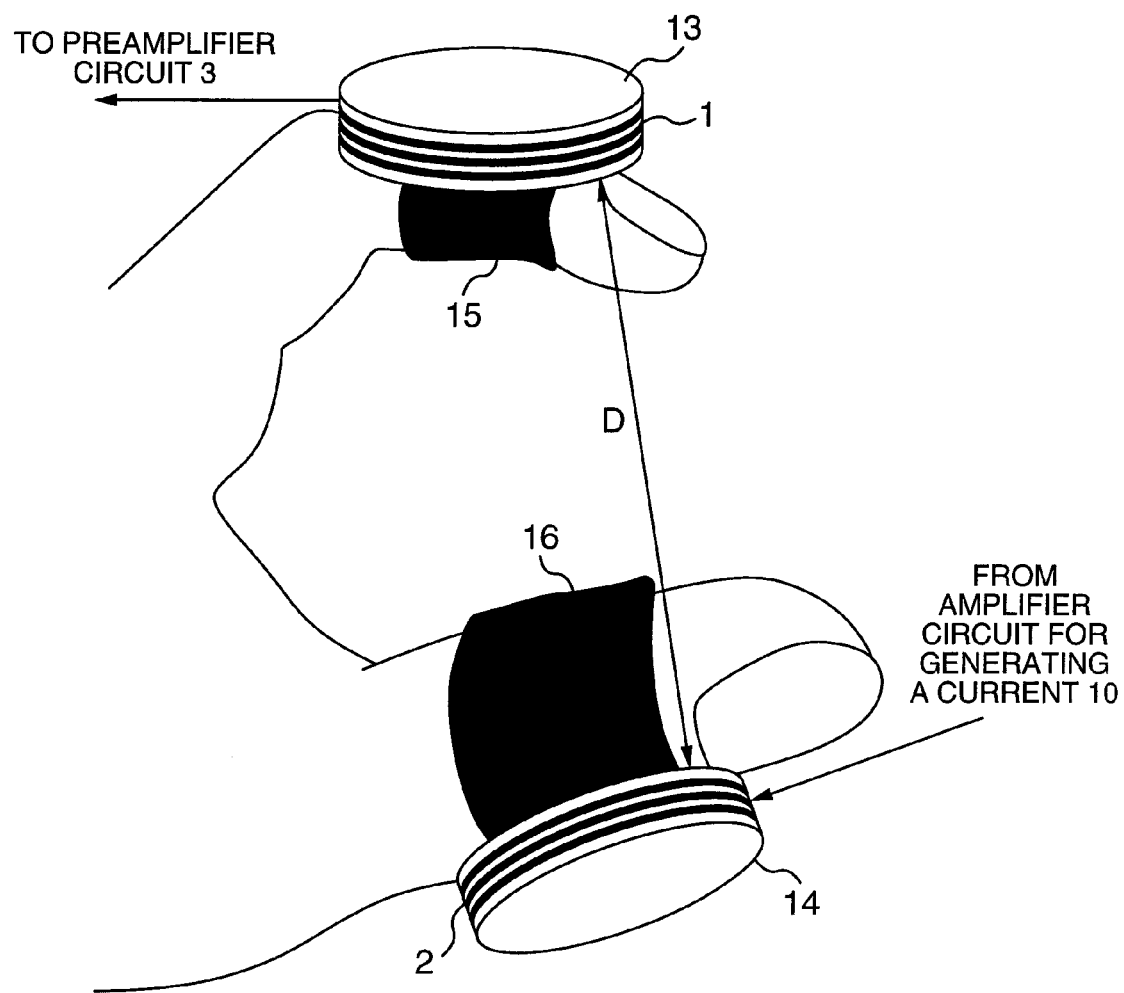
FIG. 3 illustrates a second method of attaching the detection coil and oscillation coil according to the embodiment of the present invention to the living body.

FIG. 3 illustrates a second method of attaching the detection coil and oscillation coil to the living body according to the embodiment of the present invention.

The oscillation coil 2 is attached on the upside of the thumb and the detection coil 1 is attached on the upside of the forefinger. The oscillation coil 2 is wound around the coil attaching member 14 and connected to the current generation amplifier 10 shown in FIG. 1. The detection coil 1 is wound around the coil attaching member 13 and connected to the preamplifier circuit 3 shown in FIG. 1. The attaching members 13 and 14 are attached to bands 15 and 16 and rubber or sponge, etc., are used so as to absorb individual differences in size (thickness) of fingers.

With the structures shown in FIG. 2 and FIG. 3, it is possible to obtain an output corresponding to the relative distance D between the thumb and forefinger. Furthermore, the fingers to which the detection coil and oscillation coil are attached are not limited to the thumb and forefinger and the detection coil and oscillation coil may be attached to any fingers. Moreover, the oscillation coil and detection coil may also be attached to the upper lip and lower lip so as to detect movement of the mouth.

Figure 4:
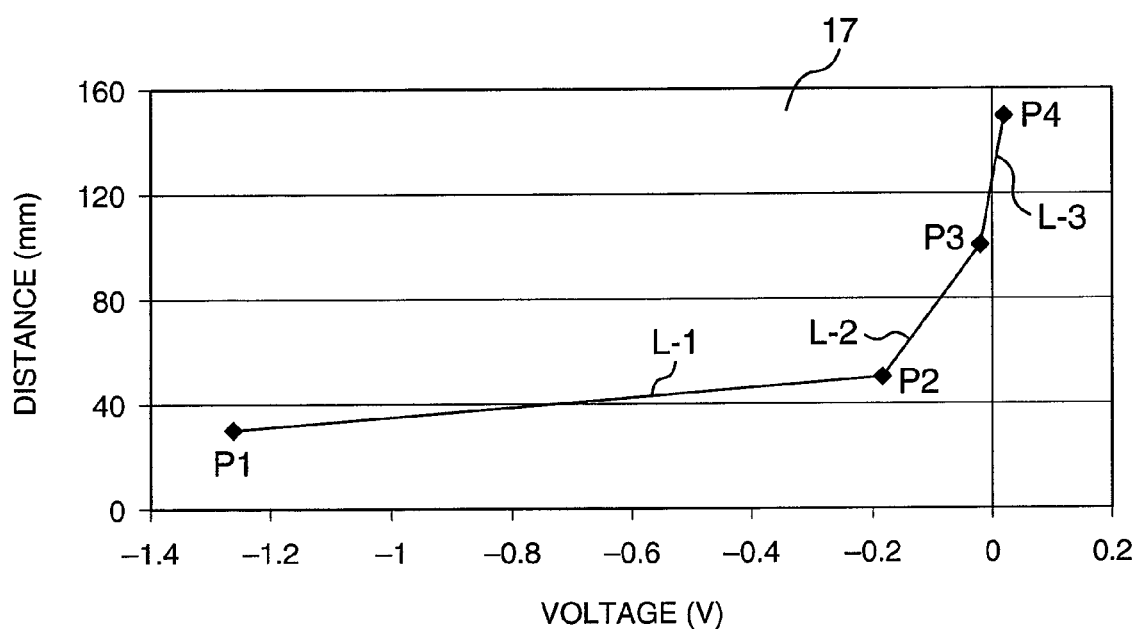
FIG. 4 illustrates an example of the result of measuring a relationship between the voltage value of the output signal 7 shown in FIG. 1 and a relative distance D between the detection coil and oscillation coil when the coils shown in FIG. 2 are attached.

Reference numeral 17 illustrates a relationship between the output signal 7 and the relative distance D and FIG. 4 illustrates an example of the result of measurement of the relationship between the voltage value of the output signal 7 shown in FIG. 1 and the relative distance D between the detection coil and oscillation coil when the coils are attached as shown in FIG. 2.

FIG. 4 shows output voltage data when the relative distance D between the detection coil and oscillation coil is 30 mm (P1), 50 mm (P2), 100 mm (P3) and 150 mm (P4). Using the data from P1 to P4, it is possible to calculate a straight line L-1 connecting P1 and P2, a straight line L-2 connecting P2 and P3 and a straight line L-3 connecting P3 and P4.

Using the straight lines (L-1, L-2, L-3), it is possible to convert the measured voltage to a distance corresponding to the relative distance D. In the example shown in FIG. 4, the relationship between the voltage value of the output signal 7 and relative distance D shown in FIG. 2 is calibrated for each examinee, but it is also possible to automatically calculate the relationship using a template of the relationship between the voltage value of the output signal 7 and relative distance D prepared beforehand. Furthermore, it is also possible to use an average of data of a plurality of examinees to create such a template of the relationship between the voltage value of the output signal 7 and relative distance D.

Figure 5A:
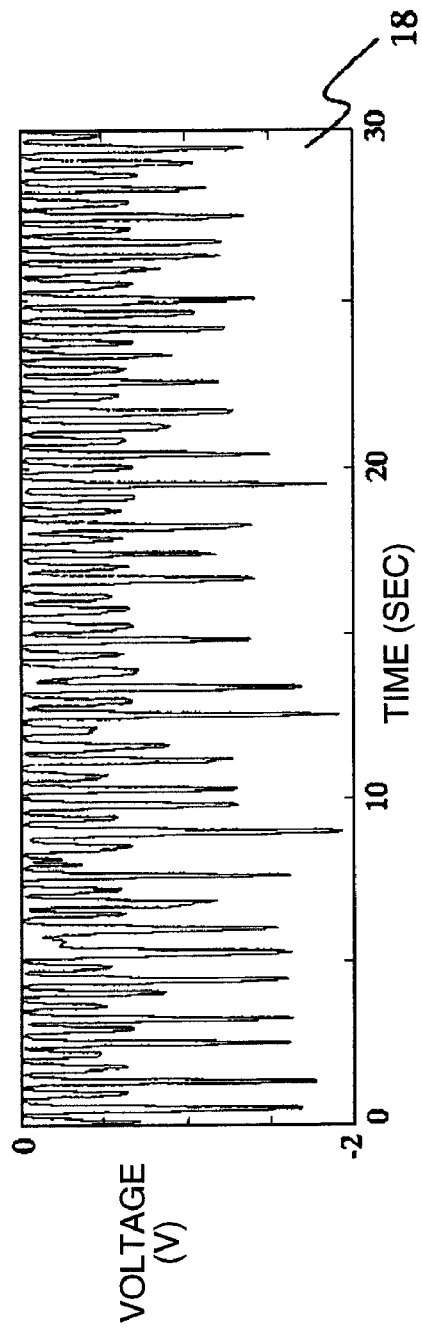
FIGS. 5A and 5B illustrate an example of the result of a conversion to a relative distance D using the straight lines L-1, L-2 and L-3 shown in FIG. 4.
Figure 5B:
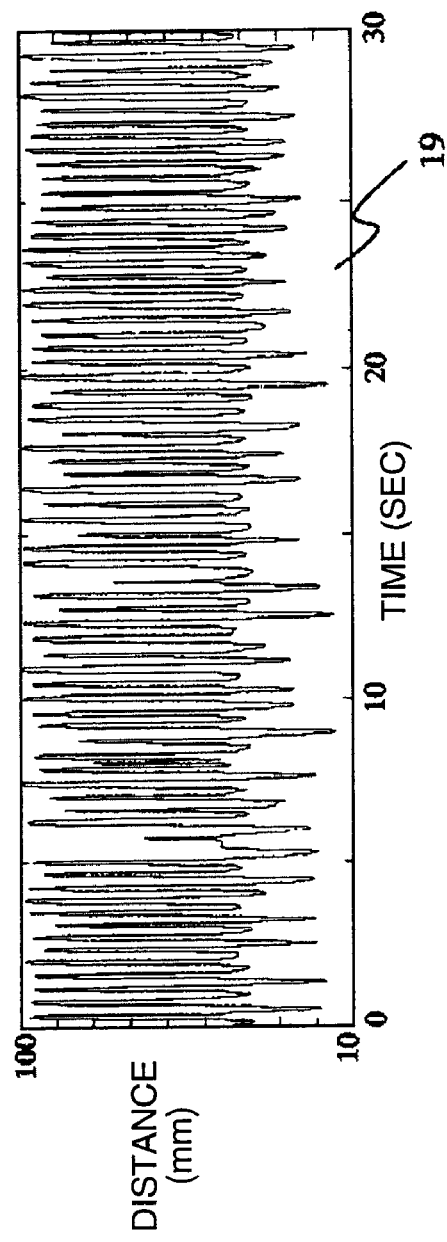

FIGS. 5A and 5B illustrate an example of the result of a conversion to the relative distance D using the straight lines L-1, L-2 and L-3 shown in FIG. 4.

The waveform in FIG. 5A shows waveforms actually obtained when a patient of Parkinson's disease is asked to do finger tapping between his/her thumb and forefinger (repeating an operation of bringing closer or separating the thumb and forefinger) as quickly and largely as possible. The time variation waveform shown in FIG. 5A shows measured data (output signal 7) 18 itself. The waveform in FIG. 5B shows data 19 which is the measured data (output signal 7) 18 converted to the relative distance D.

While detailed waveform variations are hardly observed in the upper part of the measured data 18 shown in FIG. 5A (close to voltage value 0), detailed waveform variations are noticeable in the converted data 19 of the relative distance D shown in FIG. 5B. That is, the effect of calibration of the measured data using the straight lines L-1, L-2 and L-3 shown in FIG. 4 can be visually recognized. However, a conversion of the output voltage to the relative distance D is not always necessary. When there is no need for a conversion to the relative distance D, it is possible not to convert the output voltage to the relative distance D shown in FIG. 4, FIGS. 5A and 5B but use the measured data 18 of the output signal 7 shown in FIG. 1 and carry out signal processing and subsequent processing shown in FIGS. 6A to 6C which will be described below. That is, it is possible to perform signal processing using the waveform 19 shown in FIGS. 6A to 6C as the measured data 18.

FIGS. 6A to 6C illustrate an example of measured data and the result of signal processing according to the embodiment of the present invention.

Reference numeral 19 denotes data (X) converted to the relative distance D, 20 denotes a velocity waveform (data of primary differential waveform (dX/dt) in the time direction of distance X), 21 denotes an acceleration waveform (data of secondary differential waveform ($d^2X/dt^2$) in the time direction of distance X). FIG. 6A shows the same waveform as the data (displacement waveform) 19 shown in FIG. 5B. FIG. 6A shows measured data (displacement waveform data 19 converted to relative distance D) X, FIG. 6B shows dX/dt data (velocity waveform 20) which is the data X primary-differentiated in the time direction and FIG. 6C shows $d^2X/dt^2$ data (acceleration waveform 21) which is the data X secondary-differentiated in the time direction.

As shown in FIGS. 6A to 6C, by simultaneously displaying waveforms of data X, dX/dt and $d^2X/dt^2$, it is possible to display information on rhythm irregularity and amplitude irregularity in a visually easy-to-understand manner. Furthermore, when it is preferred to reduce influences of noise included in the measured data 19(X), it is possible to use digital low pass filter processing and moving averaging processing, etc., to smooth the waveform of the measured data 19(X) for signal processing.

Figures 7A, 7B, 7C:
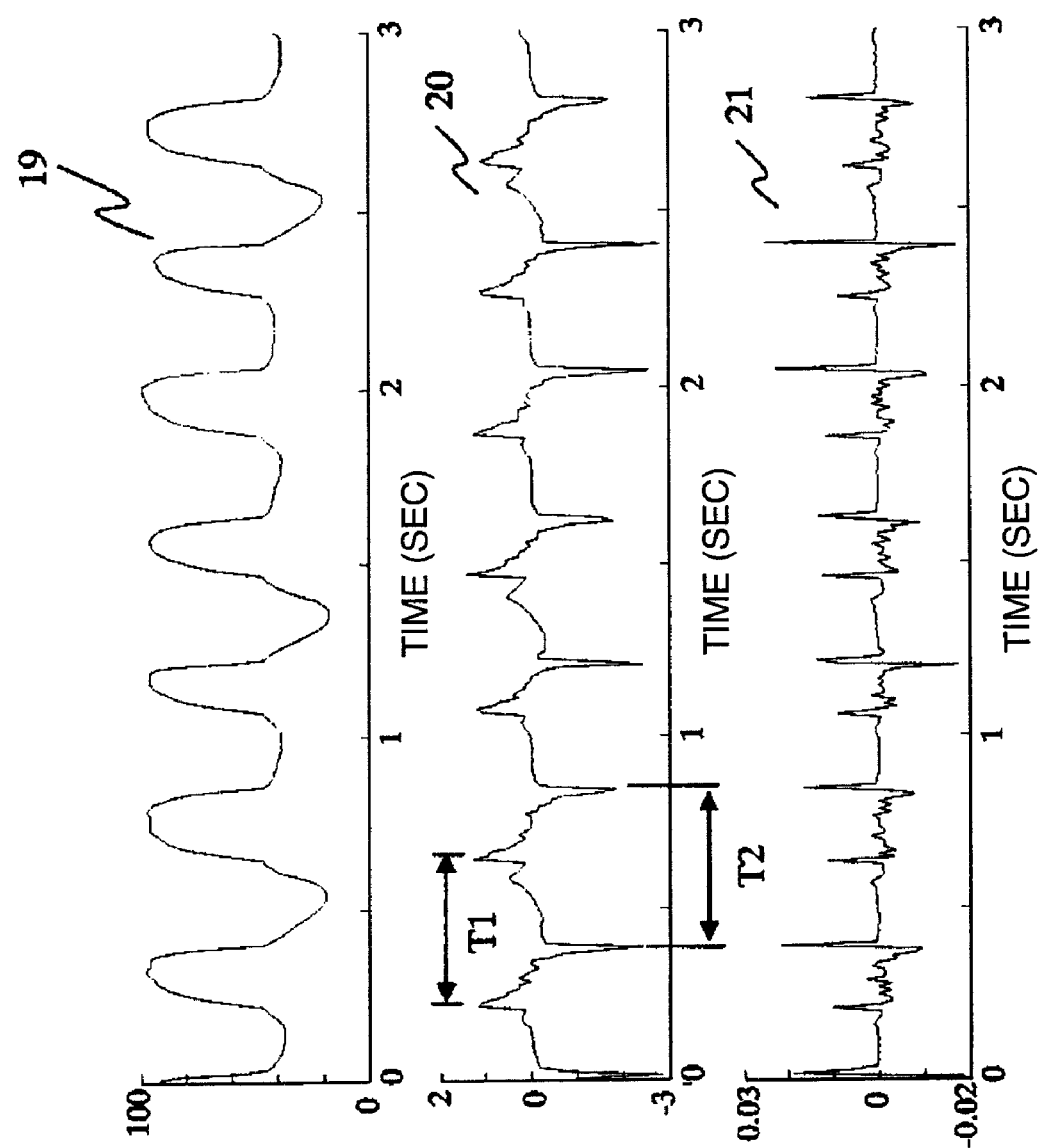
FIGS. 7A to 7C show enlarged views of a period of time from 0 to 3 seconds of FIGS. 6A to 6C.

FIGS. 7A to 7C are enlarged views of a period of time from 0 to 3 seconds in FIGS. 6A to 6C. FIG. 7A shows the measured data X 19, FIG. 7B shows the velocity waveform 20 and FIG. 7C shows the acceleration waveform 21. T1 shown in FIG. 7B denotes a time width corresponding to the time difference between detected adjacent maximum peaks of the velocity waveform and T2 shown in FIG. 7C denotes a time width corresponding to the time difference between detected adjacent minimum peaks of the velocity waveform.

A velocity waveform is used to measure timing of finger tapping. As is clear from the waveform shown in FIG. 7B, sharp peaks appear in the velocity waveform at times at which movement of the finger is rapid, and therefore it is relatively easy to detect peaks.

Figure 8A:
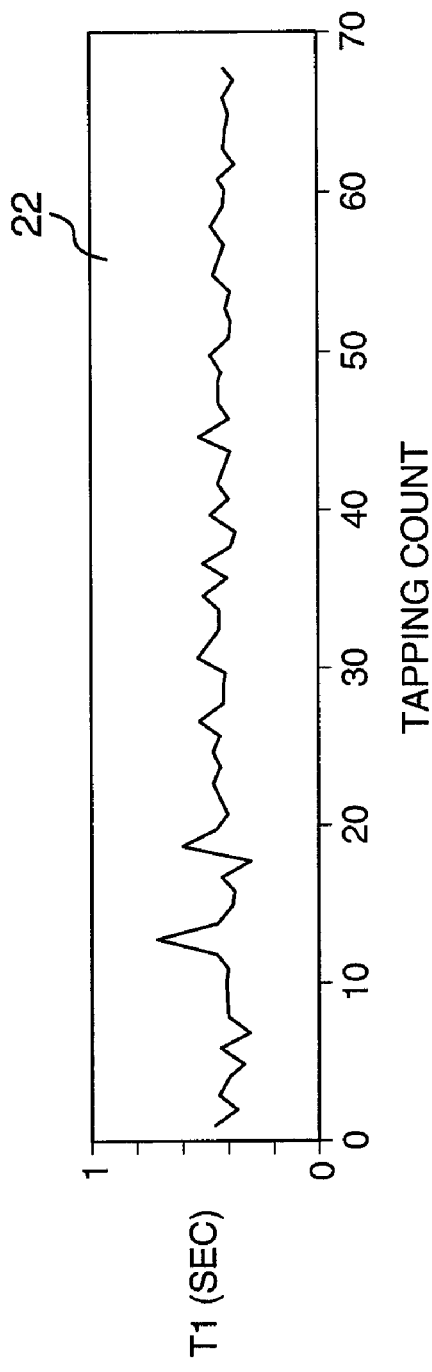
FIGS. 8A and 8B illustrate time intervals of tapping according to the embodiment of the present invention.
Figure 8B:
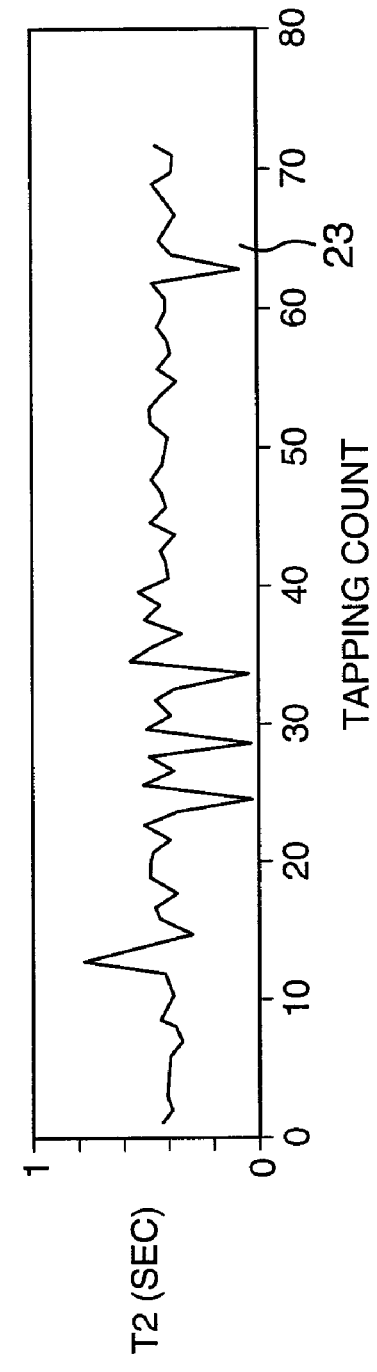

Reference numeral 22 denotes the plotting of a time variation of T1, 23 denotes plotting of a time variation of T2. FIGS. 8A and 8B illustrate time intervals of tapping according to the embodiment of the present invention. FIG. 8A illustrates the plotting of the T1 shown in FIG. 7B versus a tapping count on the horizontal axis and FIG. 8B illustrates the plotting of the T2 shown in FIG. 7B versus a tapping count on the horizontal axis. In FIGS. 8A and 8B, the horizontal axis shows a tapping count, but it is also possible to show a time on the horizontal axis. The figures show that T1 varies with finger tapping centered on 0.4 seconds. On the other hand, T2 varies centered on substantially 0.4 seconds as with T1, but several fluctuations are observed. As shown in FIGS. 8A and 8B, the plotting of time variations of tapping allows time fluctuations of tapping to be visually understood.

FIGS. 9A to 9C illustrate a technique of detecting amplitude irregularity of tapping using the distance waveform according to the embodiment of the present invention. FIG. 9A shows the measured data X19 shown in FIG. 7A, FIG. 9B shows the velocity waveform 20 shown in FIG. 7B and FIG. 9C shows the acceleration waveform 21 shown in FIG. 7C.

As shown in FIGS. 9A to 9C, within the time zone between a maximum timing (e.g., Tu1) and the next timing (e.g., Tu2) of the tapping velocity obtained from the velocity waveform shown in FIG. 7B, a timing at which a maximum distance of the measured data 19(X) is indicated (e.g., tu1) is detected. Likewise, tu2 is detected between Tu2 and Tu3, tu3 is detected between Tu3 and Tu4, tu4 is detected between Tu4 and Tu5, tu5 is detected between Tu5 and Tu6, tu6 is detected between Tu6 and Tu7 and tu7 is detected between Tu7 and Tu8 (not shown). Furthermore, within the time zone between a minimum timing (e.g., Td1) and the next timing (e.g., Td2) of the tapping velocity obtained from the velocity waveform shown in FIG. 7B, a timing at which a minimum distance of the measured data 19(X) is indicated (e.g., td1) is detected. Likewise, td2 is detected between Td2 and Td3, td3 is detected between Td3 and Td4, td4 is detected between Td4 and Td5, td5 is detected between Td5 and Td6, td6 is detected between Td6 and Td7 and td7 is detected between Td7 and Td8 (not shown). A maximum peak value of the distance (from tu1 to tu7 in FIGS. 9A to 9C) and a minimum peak value (from td1 to td8 in FIGS. 9A to 9C) are detected within the entire measuring time.

Then, a maximum value 24 is detected from a data group of maximum peak values (from tu1 to tu7 in FIGS. 9A to 9C). Furthermore, a minimum value 25 is detected from a data group of minimum peak values (from td1 to td8 in FIGS. 9A to 9C). A distance difference (ΔMAX) 26 between the maximum value 24 and minimum value 25 is calculated. When the maximum value 24 is considered as a reference, a threshold of 30% of the distance difference (ΔMAX)26 is expressed as a dashed line 27-1, a threshold of 50% of the distance difference (ΔMAX)26 is expressed as 27-2, a threshold of 70% of the distance difference (ΔMAX)26 is expressed as 27-3 and a threshold of 90% of the distance difference (ΔMAX)26 is expressed as 27-4.

In order to express the amplitude irregularity of minimum peaks (from td1 to td8) in a numerical form, this embodiment detects the number of minimum peaks falling below this threshold. For example, in the case of the example shown in FIG. 9A, three minimum peaks td2, td4 and td7 fall below the threshold of 90%, six minimum peaks td1, td3, td4, td5, td7 and td8 fall below the threshold of 70% and eight minimum peaks td1, td2, td3, td4, td5, td6, td7 and td8 fall below the thresholds of 50% and 30%. It is possible to calculate the tapping probability from the detected count as (detected count)/(total tapping count). For example, in the above described example, since three peaks fall below the threshold of 90%, the probability is count 3 divided by total count 8, that is, 37.5% (3/8). Likewise, with regard to maximum peaks tu1 to tu7, too, a threshold is set relative to the minimum value 25 and the number of maximum peaks exceeding the threshold is detected.

FIG. 10 shows an example of the display screen showing amplitude irregularity according to the embodiment of the present invention. As shown in FIG. 10, a tapping probability 29 (detected count)/(total tapping count) is displayed for the threshold 28 of each amplitude. From the display in FIG. 10, it is possible to check the probability of a successful tapping count and provide quantitative diagnostics.

FIG. 11 shows an example of the display screen of average tapping intensity according to the embodiment of the present invention. FIG. 11 shows a calculation expression 30 of average tapping intensity. Though each item is not expressed as a numerical value in FIG. 11, when average tapping intensity is shown on the display screen, the value of each item is shown. By calculating a total area within the measurement time of the acceleration waveform shown in FIG. 6C, it is possible to calculate the average tapping intensity as (total area of acceleration waveform/total tapping count). From the calculation or display in FIG. 11, it is possible to simply express the state in which the tapping count is sufficient but the tapping force is insufficient (with small amplitude) in a numerical form and thereby provide quantitative diagnostics.

Figure 12:
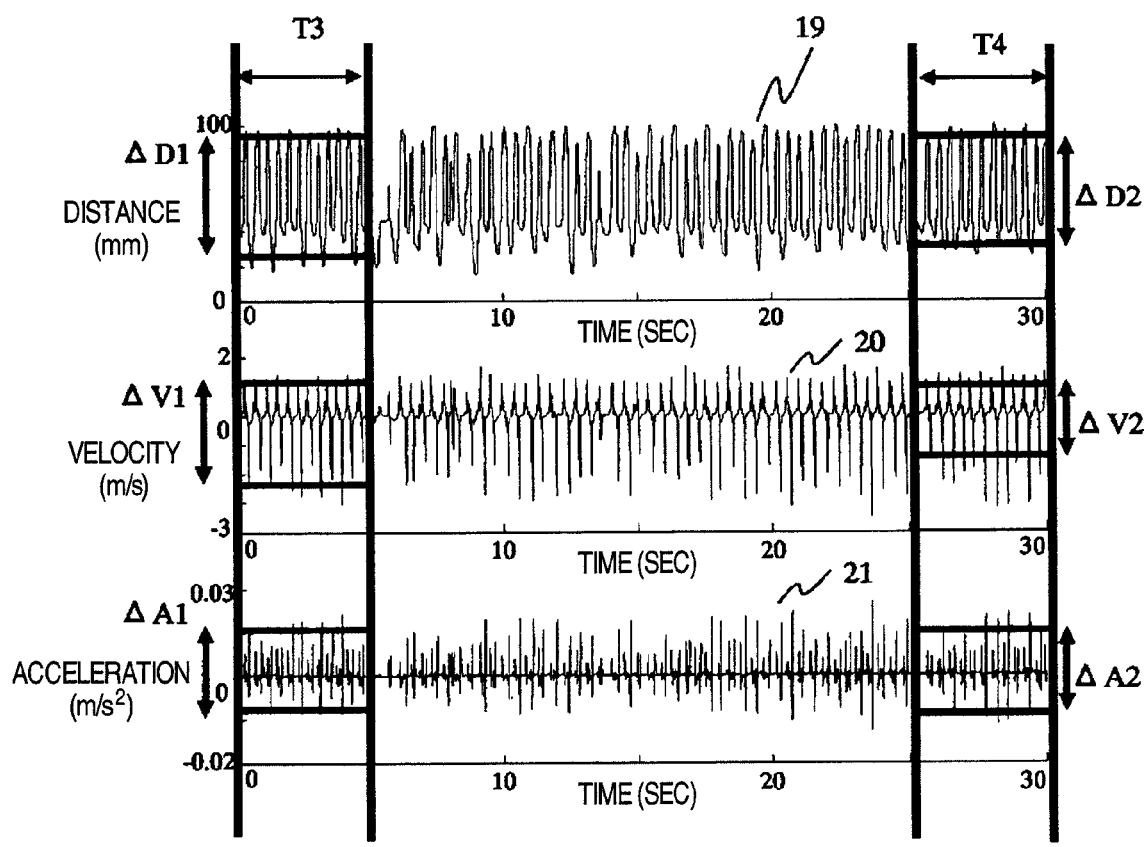
FIG. 12 illustrates a method of digitalization for evaluating the process of stiffness (hesitation) of movement of fingers over time according to the embodiment of the present invention.

FIG. 12 illustrates a technique of expressing in a numerical form an evaluation of the stiffening (hesitation) process of movement of fingers over time according to the embodiment of the present invention. The top row in FIG. 12 shows the measured data 19 shown in FIG. 6A, the middle row in FIG. 12 shows the velocity waveform 20 shown in FIG. 6B and the bottom row in FIG. 12 shows the acceleration waveform 21 shown in FIG. 6C.

Two time zones, that is, the first and last time zones are selected (T3 and T4 are selected in FIG. 12) from the measurement time, average intensity of maximum peak values (tu1 to tu7 shown in FIG. 9A) and average intensity of minimum peak values (td1 to td8 shown in FIG. 9A) of tapping in the time zones T3 and T4 are calculated and a difference between average intensity of the maximum peaks and average intensity of the minimum peaks is calculated. The difference in average intensity is calculated from each waveform, and for example, ΔD1, ΔD2, ΔV1, ΔV2, ΔA1, ΔA2 can be detected. Though not shown in FIG. 12, it is also possible to show values of ΔD1, ΔD2, ΔV1, ΔV2, ΔA1 and ΔA2 on the display screen in FIG. 12.

Figures 13, 14:
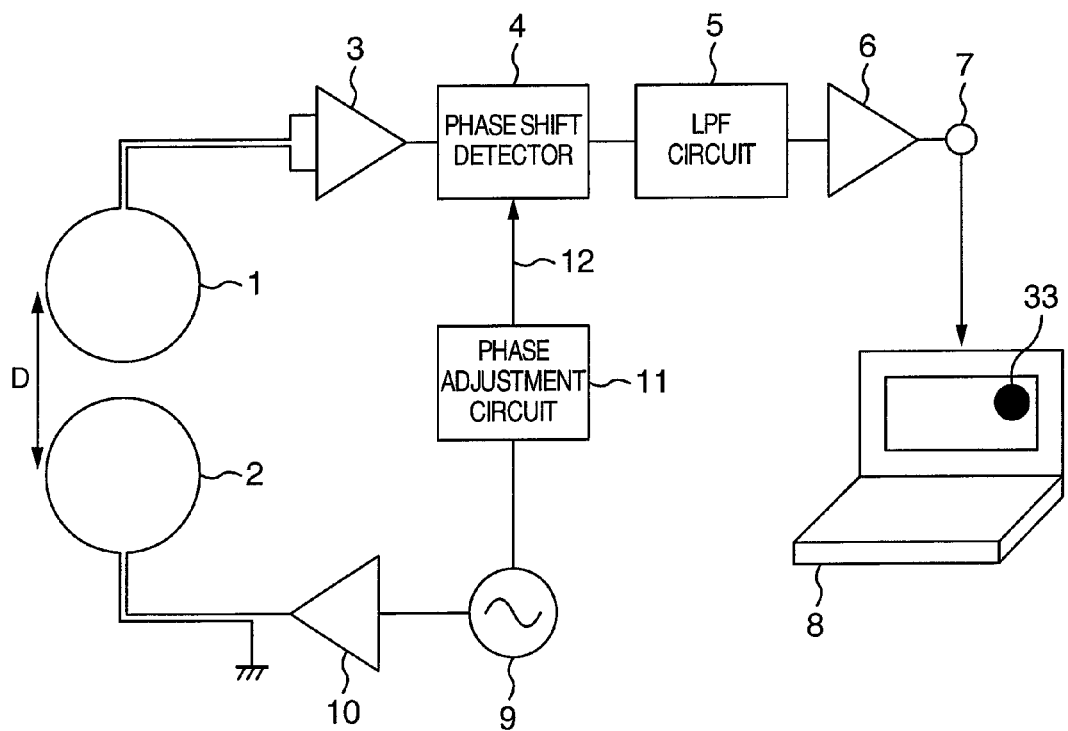
FIG. 13 illustrates an example of the display screen showing a hesitation rate according to the embodiment of the present invention.
FIG. 14 illustrates a system configuration provided with a function of evaluating a tracking characteristic of tapping according to the embodiment of the present invention.

FIG. 13 illustrates an example of the display screen showing a hesitation rate according to the embodiment of the present invention. Reference numeral 31 denotes a screen showing parameters and 32 denotes a screen showing hesitation rates. FIG. 13 shows hesitation rates (ΔD2/ΔD1, ΔV2/ΔV1 and ΔA2/ΔA1) in percentage calculated based on the values of ΔD1, ΔD2, ΔV1, ΔV2, ΔA1 and ΔA2 obtained from FIG. 12. The display in FIG. 12 makes it possible to quantitatively evaluate the degree of "hesitation (state in which stiffness of movement worsens gradually)" of tapping.

FIG. 14 illustrates a system configuration provided with a function of evaluating a tracking characteristic of tapping according to the embodiment of the present invention. Reference numeral 33 denotes a blinking display for indicating a tapping rhythm.

Figure 15:
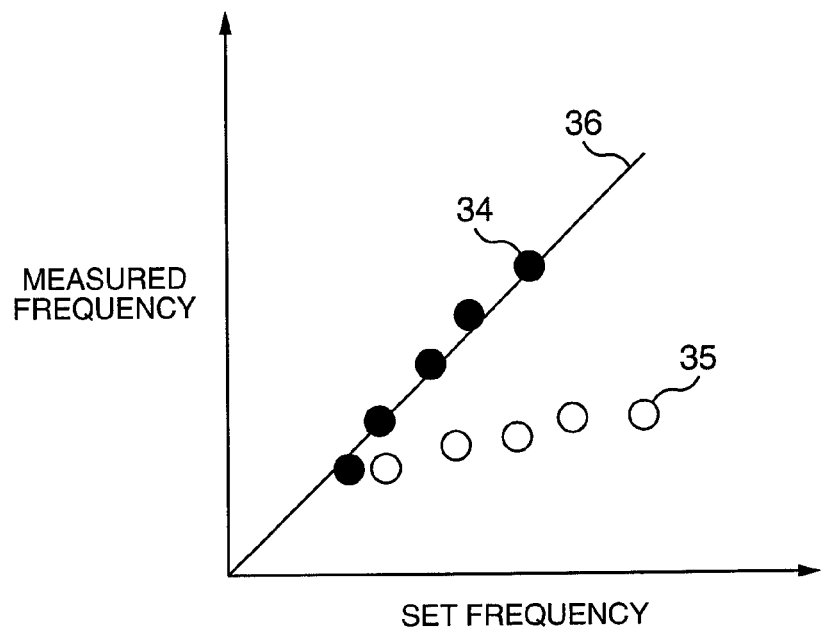
FIG. 15 illustrates a display screen for checking whether finger tapping can be performed by following a set frequency according to the embodiment of the present invention.

In the configuration shown in FIG. 14, the display 33 indicating the rhythm of tapping which the examinee is asked to do in the configuration shown in FIG. 1 is shown on the computer 8. The examinee does finger tapping to the tapping rhythm on the display 33. An inspection is carried out by changing the timing frequency of the tapping rhythm shown on the display 33 and the result is as shown in FIG. 15, which will be described below. Instead of the display 33, it is also possible to transmit the timing of the tapping rhythm to the examinee by means of a beep sound generated by beep generating means.

FIG. 15 illustrates a display screen for checking whether finger tapping can be performed following a set frequency according to the embodiment of the present invention. The horizontal axis in FIG. 15 shows a set frequency. The main frequency of actually measured tapping is detected through a fast Fourier transform, etc., and plotted on the vertical axis in FIG. 15 as the measured frequency. For example, black bullets 34 show a result of a healthy person and white bullets 35 show a result of a patient of Parkinson's disease. It is visually recognized that while the black bullets 34 are located close to a target tracking straight line 36 (straight line showing a proportion relationship), the bullets of Parkinson's disease (white bullets 35) are deviated from the target tracking straight line 36 (straight line showing a proportion relationship).

Figure 16:
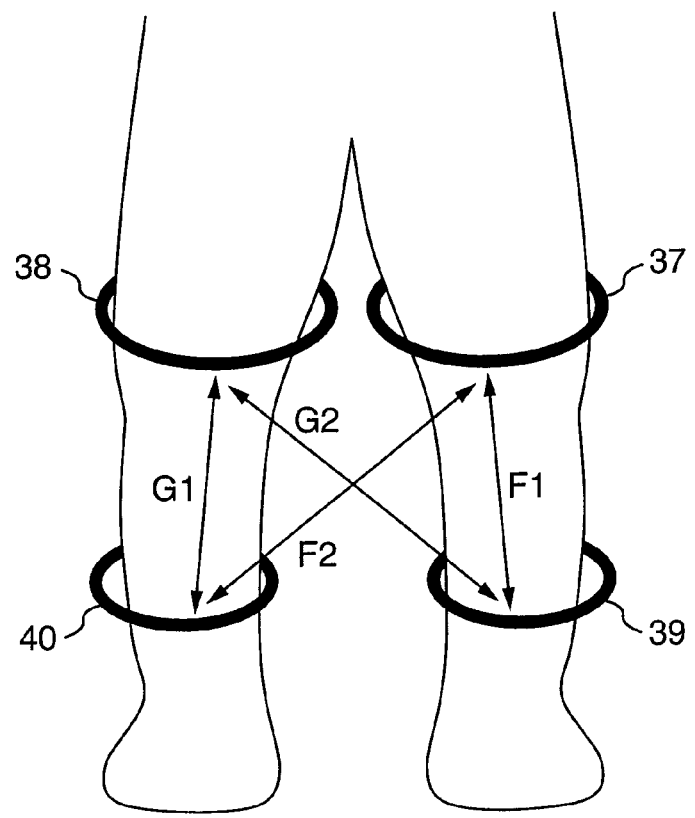
FIG. 16 illustrates a configuration of a plurality of oscillation coils and a plurality of detection coils attached to both legs according to the embodiment of the present invention.

FIG. 16 illustrates a configuration of a plurality of oscillation coils and a plurality of detection coils attached to both legs according to the embodiment of the present invention.

An oscillation coil 37 is oscillated at a predetermined oscillation frequency of f1 and attached to the left thigh. Likewise, an oscillation coil 38 is oscillated at a predetermined oscillation frequency of f2 and attached to the right thigh. Furthermore, a detection coil 39 detects the predetermined frequencies f1 and f2 independently of each other and can thereby measure physical quantities corresponding to relative distances F1 and G2 simultaneously. Likewise, a detection coil 40 detects the predetermined frequencies f1 and f2 independently of each other and can thereby measure physical quantities corresponding to relative distances G1 and F2 simultaneously. According to the configuration shown in FIG. 16, it is possible to inspect a walking speed, etc., during a walk and quantify coordinated movement between two regions of the living body as with finger tapping.

Figure 17:
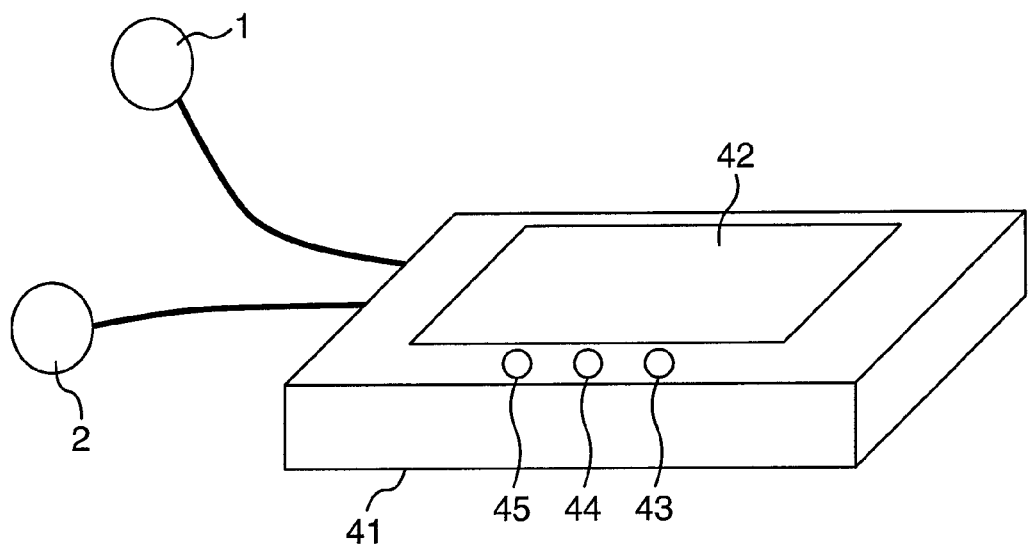
FIG. 17 illustrates a block diagram of a measuring system with components assembled into one body according to the embodiment of the present invention.

FIG. 17 illustrates a block diagram of a measuring system with components assembled into one body according to the embodiment of the present invention. In the example shown in FIG. 17, parts other than the detection coil 1 and oscillation coil 2 shown in FIG. 1 or FIG. 14 are assembled into one body as a main apparatus 41. The main apparatus 41 incorporates the preamplifier circuit 3, the phase shift detector 4, the low pass filter (LPF) circuit 5, the amplifier circuit 6, the computer 8, the AC generation circuit 9, the current generation amplifier circuit 10 and the phase adjustment circuit 11.

The main apparatus 41 is provided with a display 42, a measurement start/stop button/power ON/OFF button 43, an indicator 44 which shows a tapping rhythm (instead of the indicator 44, it is also possible to use means for generating beep sound and transmitting a timing of the tapping rhythm to an examinee) and a display mode selection button 45.

The display 42 can display various waveforms and parameters shown in FIGS. 6A to 6C, FIGS. 8A and 8B, FIG. 10, FIG. 11, FIG. 13 and FIG. 15, etc., and the display mode selection button 45 can select a screen to be displayed. Furthermore, the indicator 44 showing the tapping rhythm allows the tracking inspection shown in FIG. 14 and FIG. 15. The detection coil 1 and oscillation coil 2 are connected to the main apparatus 41 from the outside. The above described configuration makes the apparatus portable, allowing it to be used for measurement at home or carried slung from a person's shoulder, etc. The main apparatus 41 can also be provided with a communication function for allowing data, etc., measured at home to be transferred to a hospital, etc.

Furthermore, the apparatus configuration shown in FIG. 17 (or FIG. 1 or FIG. 14) can also be adapted so as to incorporate the output signal 7 in FIG. 1 or FIG. 14, means for transmitting analog data or digital data displayed on the display 42 in FIG. 17 by radio or means for transmitting data through a local area network (LAN) or telephone line, etc., to construct a network system capable of collecting data remotely. Once such a network system is constructed, it is possible to monitor coordinated movement of a living body on a 24-hour basis and produce the effect of being able to control daily variations of Parkinson's disease more accurately.

In addition to the method of observing the degree of tapping through finger tapping, Parkinson's disease can also be examined by observing a symptom called "rigidity" which hardens bending and stretching of arms. "Rigidity" is an important factor in deciding the severity of Parkinson's disease.

Figure 18:
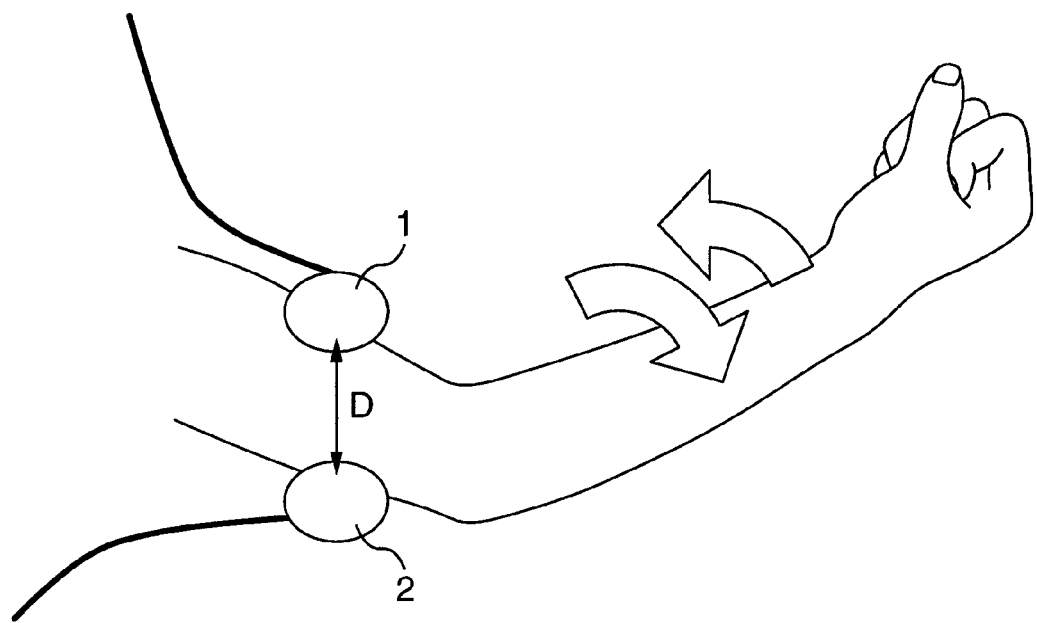
FIG. 18 illustrates a configuration example of the embodiment of the present invention attached to an arm for "rigidity" monitoring.

FIG. 18 illustrates a configuration example of the embodiment of the present invention attached to an arm for "rigidity" monitoring. With the detection coil 1 and oscillation coil 2 fixed at two positions of an arm using a rubber member, it is possible to detect a distance D when the arm is bent and stretched in the same circuit configuration as that in FIG. 1.

Figure 19:
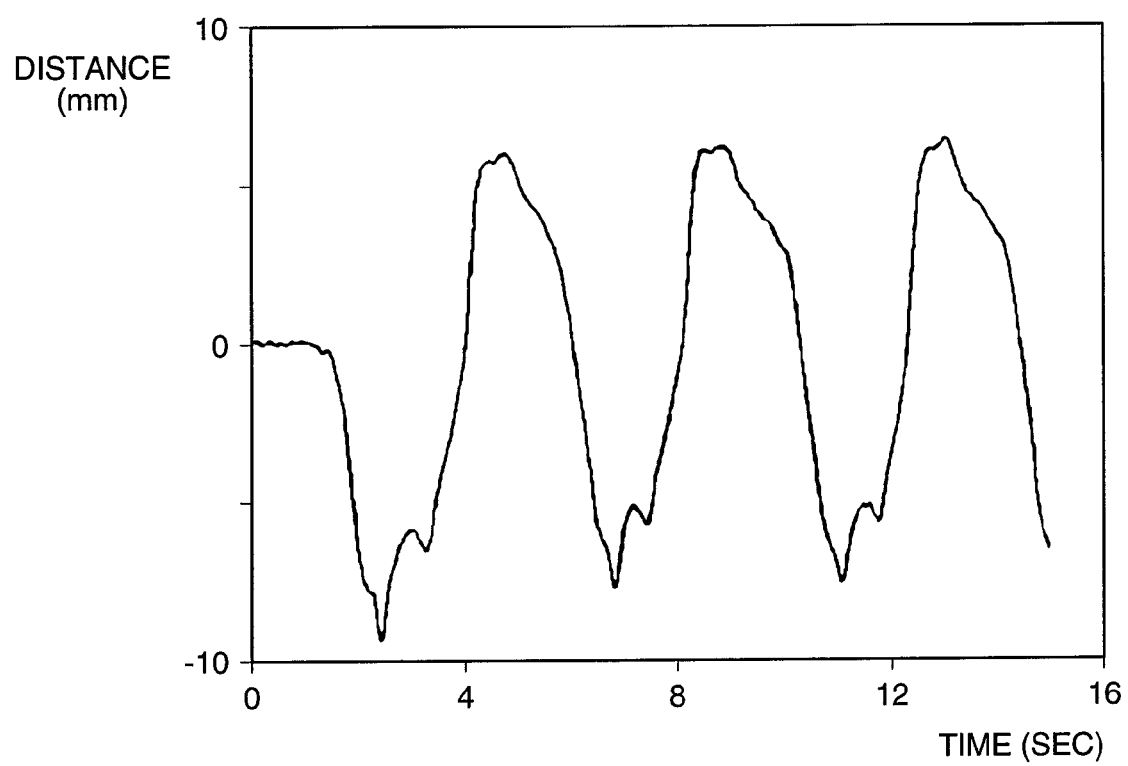
FIG. 19 illustrates an example of the result of measurement with the embodiment of the present invention actually attached to the arm.

FIG. 19 illustrates an example of the result of measurement with the embodiment of the present invention actually attached to the arm. FIG. 19 shows the result of measurement of an able-bodied person when his/her arm is bent and stretched three times every 15 seconds. The result shown in FIG. 19 is calibrated considering the position when the arm is stretched as 0 mm. With Parkinson's disease, several time zones of slow movement appear during this bending/stretching operation, making it possible to evaluate the severity of the Parkinson's disease. It goes without saying that it is also possible to apply primary differentiation and secondary differentiation to the measured waveform shown in FIG. 19 and create a velocity waveform and acceleration waveform as shown in FIGS. 6A to 6C.

According to the living body inspection apparatus of the present invention, it is possible to quantitatively measure physical quantities corresponding to a relative distance between two regions of a living body, continuously detect signals indicating movements (coordinated movement) of two or more regions of the living body and thereby quantify the coordinated movement. Therefore, it is possible to quantitatively determine the motor function accompanying cerebropathy such as Parkinson's disease.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. A living body inspection apparatus comprising:
   an AC generation circuit which generates an AC voltage having a predetermined frequency;
   converting means for converting said AC voltage output from said AC generation circuit to an AC current;
   an oscillation coil which passes said AC current output from said converting means;

a detection coil which detects an AC magnetic field generated from said oscillation coil;
an amplification circuit which amplifies a voltage generated by the magnetic field induced by said detection coil;
detecting means for detecting an output signal of said amplification circuit with a predetermined frequency;
a low pass filter to which an output signal of said detecting means is input;
means for setting said oscillation coil in a first region of a living body;
means for setting said detection coil in a second region of said living body;
recording means for recording an output of said low pass filter while said first region and said second region of said living body are moving;
displaying means for displaying data recorded in said recording means or results of analysis of recorded data; and
transmitting means for transmitting a tapping timing to an examinee.

2. The living body inspection apparatus according to claim 1, wherein said detecting means detects the output signal of said amplification circuit with the same frequency as that of said AC generation circuit or a double harmonic frequency.

3. The living body inspection apparatus according to claim 1, further comprising means for detecting a tapping frequency as a measurement frequency, wherein a set frequency set in said transmitting means and said measurement frequency are displayed.

4. The living body inspection apparatus according to claim 1, wherein said output of said low pass filter is an output which changes depending on a variety of a relative distance between said first region and said second region while said first region and said second region of said living body are moving.

5. A living body inspection apparatus comprising:
an AC generation circuit which generates an AC voltage having a predetermined frequency;
converting means for converting said AC voltage output from said AC generation circuit to an AC current;
an oscillation coil which passes said AC current output from said converting means;
a detection coil which detects an AC magnetic field generated from said oscillation coil;
an amplification circuit which amplifies a voltage generated by the magnetic field induced by said detection coil;
detecting means for detecting an output signal of said amplification circuit with the same frequency as that of said AC generation circuit or a double harmonic frequency;
a low pass filter to which an output signal of said detecting means is input;
means for setting said oscillation coil on a leg of a living body;
means for setting said detection coil on said leg of said living body;
recording means for recording an output of said low pass filter while said leg is moving; and
displaying means for displaying data recorded in said recording means or results of an analysis of said recorded data.

6. The living body inspection apparatus according to claim 5, further comprising said oscillation coil being set on a right leg or a left leg of said living body and said detection coil being set on a right leg or a left leg of said living coil.

7. A living body inspection apparatus comprising:
an AC generation circuit which generates an AC voltage having a predetermined frequency;
converting means for converting said AC voltage output from said AC generation circuit to an AC current;
an oscillation coil which passes said AC current output from said converting means;
a detection coil which detects an AC magnetic field generated from said oscillation coil;
an amplification circuit which amplifies a voltage generated by the magnetic field induced by said detection coil;
detecting means for detecting an output signal of said amplification circuit with the same frequency as that of said AC generation circuit or a double harmonic frequency;
a low pass filter to which an output signal of said detecting means is input;
means for setting said oscillation coil in a first region of a living body;
means for setting said oscillation coil in a second region of said living body;
recording means for recording an output of said low pass filter while said first region and said second region of said living body are moving; and
displaying means for displaying data recorded in said recording means or results of an analysis of recorded data,
wherein said living body inspection apparatus is provided with a main apparatus which houses said AC generation circuit, said converting means, said amplification circuit, said detecting means, said low pass filter, said recording means and said displaying means.

* * * * *